United States Patent [19]

Russ

[11] 4,045,139
[45] Aug. 30, 1977

[54] COMPACT PORTABLE CONTAMINATED FUEL DETECTOR WITH HAND-OPERATED PUMP

[75] Inventor: Daniel G. Russ, Fort Wayne, Ind.

[73] Assignee: Telectro-Mek, Inc., Fort Wayne, Ind.

[21] Appl. No.: 671,309

[22] Filed: Mar. 29, 1976

[51] Int. Cl.² .................. G01N 1/00; G01N 15/00
[52] U.S. Cl. .................................. 356/36; 73/61 R; 356/38; 356/72
[58] Field of Search ............ 356/36, 38, 72, 73; 73/61 R, 425.6

[56] References Cited
U.S. PATENT DOCUMENTS

| | | | |
|---|---|---|---|
| 2,889,736 | 6/1959 | Borg | 73/61 R |
| 3,010,583 | 11/1961 | Kenyon | 73/61 R |
| 3,184,122 | 5/1965 | Nerenberg | 73/425.6 |
| 3,401,591 | 9/1968 | Anthon | 356/36 |
| 3,582,768 | 6/1971 | Watson et al. | 356/72 |

OTHER PUBLICATIONS

Millipore; Analysis & Control of Contamination in Aviation Fuels; Received Jan. 22, 1968.

Primary Examiner—Vincent P. McGraw
Attorney, Agent, or Firm—Dorfman, Herrell and Skillman

[57] ABSTRACT

A portable, lightweight, compact contaminated fuel detector uses a standard batch sampling technique. This is done through two series filters in a filter holder into a vacuum receptacle. The differential filter opacity is checked in a photocell fixture using a light whose intensity is first adjusted by potentiometer to a standard level using a milliammeter which is also read to determine each filter opacity. The compactness and weight reduction is accomplished using a lightweight box enclosure with a supporting deck carrying equipment including a hand-operated vertically oriented vacuum pump and careful arrangement of the pump within the enclosure relative to other elements of the system.

4 Claims, 6 Drawing Figures

COMPACT PORTABLE CONTAMINATED FUEL DETECTOR WITH HAND-OPERATED PUMP

The present invention concerns a lightweight compact highly portable contaminated fuel detector which can be readily carried into and used for checking fuel in remote and out of the way locations. The detector can be used completely without the need of an electrical power source and eliminates any danger of explosion.

The practice of checking fuels for contamination has become increasingly important as fuels and engines become more sophisticated. Various means of checking for contaminants exists. A preferred method relies upon the removal of a measured sample from a storage or use container so that it can be tested as a batch completely outside any system or process using the fuel. Such a method is described in Morton Moul's U.S. Pat. No. 3,063,289. Such batch testing offers great advantages and is the area of consideration of the present invention.

Most prior art contaminated fuel detectors are relatively large and, because of size, arrangement and nature of components often provides a bulky, heavy, unwieldy package which is inconvenient to carry by hand into remote locations. Furthermore, contaminated fuel detectors require power for motors to drive vacuum pumps and to run testing circuits such as the light source and photoelectric detector and meter in a detection circuit.

The present invention obviates many of these problems and provides a lightweight portable, compact, easily handled, completely self-contained contaminated fuel detector. It substitutes a hand-operated vacuum pump for an electrical pump, and, by efficiency in arrangement, reduces the size and bulk of various components. In addition to reducing weight and size by eliminating electrical motors, the need for expensive and hard to procure explosion proof motors is obviated and the device is far more foolproof than any device which might contain a motor. Furthermore, the design of the circuits and equipment to use lightweight batteries eliminates the need for any outside power. The provision for battery clips for retaining batteries automatically connected in the various circuits makes battery operation and maintenance elementary.

More specifically, the present invention represents an improvement in contaminated fuel detectors employing at least sample holder means, fuel filter means in a filter retainer, and a vacuum receptacle arranged in series, with means drawing a vacuum causing said parts to seal together and accelerate flow of fuel through the filter means into the vacuum fuel receptacle. Vacuum pump means for said purpose is connected by a vacuum line to said vacuum receptacle. The invention relates to an improvement wherein the contaminated fuel detector is contained within a boxed enclosure including a top and a bottom. A deck is supported on the bottom and supports, in turn, a photocell comparator, a meter coupled thereto, the vacuum chamber and vacuum pump. The vacuum pump is a hand-operated pump, including a vertically oriented cylinder parallel to and adjacent to the vacuum receptable and containing a vertically movable piston with an axially arranged piston rod. Sealing means is provided between the cylinder and the edge of the piston. Check valves are provided between the vacuum chamber and vacuum pump, preventing air return to the vacuum chamber, and at the outlet, preventing air return to the pump. The deck supports removable pieces such as the filter retainer and sample holder. The top provides a cover enclosing parts projecting above the deck and may provide storage for spare parts and loose auxiliary equipment.

For a better understanding of the present invention reference is made to the drawings in which.

Figure 1:
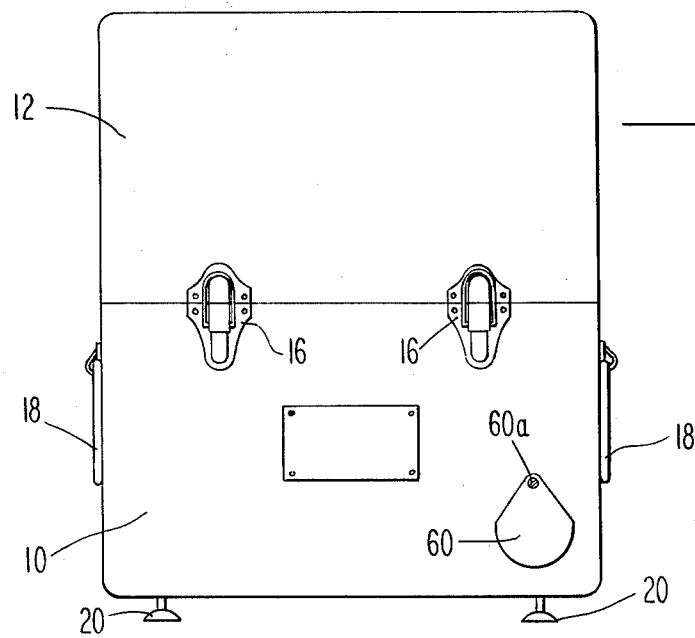
FIG. 1 is a front elevational view of the portable contaminated fuel detecting unit with the cover closed.
Figure 2:
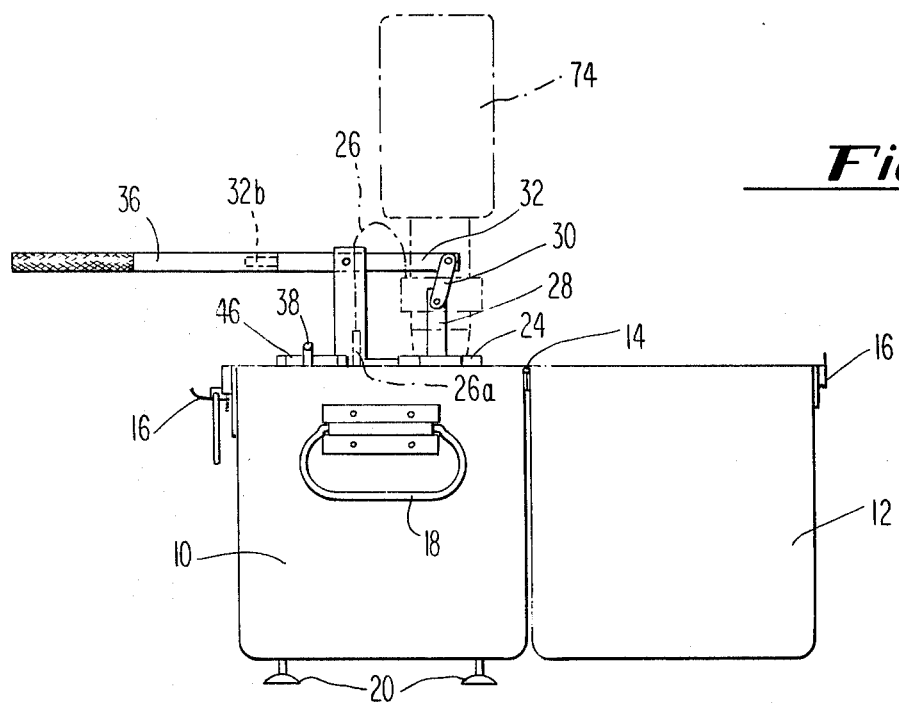
FIG. 2 is a side elevational view of the same unit with the hinged cover open, the sample bottle and filter unit in operating position, and the pump handle extension in place.

Referring first to FIGS. 1 and 2, it will be observed that a preferred embodiment of the contaminated fuel detector of the present invention is enclosed in a housing consisting of a pair of deep hollow boxes 10, 12 of essentially the same dimensions with one side open connected together with their open sides facing one another at the back of the housing by hinge means 14 which permits opening of the cover 12 as shown in FIG. 2. The casing is preferably provided with a pair of manually actuated latches 16 which permit the top 12 and bottom 10 to be opened for use and firmly closed for carrying. Handles 18 are attached to the sides of bottom box 10 to facilitate carrying. When the device is in use, it rests on four suction cup feet 20 attached to the bottom of the housing box 10 and permitting the unit to be attached temporarily to a flat surface to provide stability needed to permit hand pumping without having to hold onto the casing.

As shown, horizontal support deck 22 (shown in FIG. 3) is removably fixed to and closes the opening of the bottom box 10, preferably right at the opening. The depth of the lower box 10 is determined largely by the size of components of the system supported by the support deck 22 and projecting down into the lower box 10. Making the upper box 12 of identical size has advantage even though the components do not project so far above the deck. This additional space is useful for storage of auxiliary equipment used in making tests, such as the sample bottle, and other equipment.

The construction shown permits a great reduction in size over other known fuel contamination detectors which have been made commercially. The version shown has been made commercially in a closed casing size having overall dimension of 14 inches high, 10 inches deep and 14 inches wide. With the components shown and described, and additional spare parts, the overall weight of the unit has been kept to 28 pounds, making it readily portable into otherwise inaccessible areas.

Figure 3:
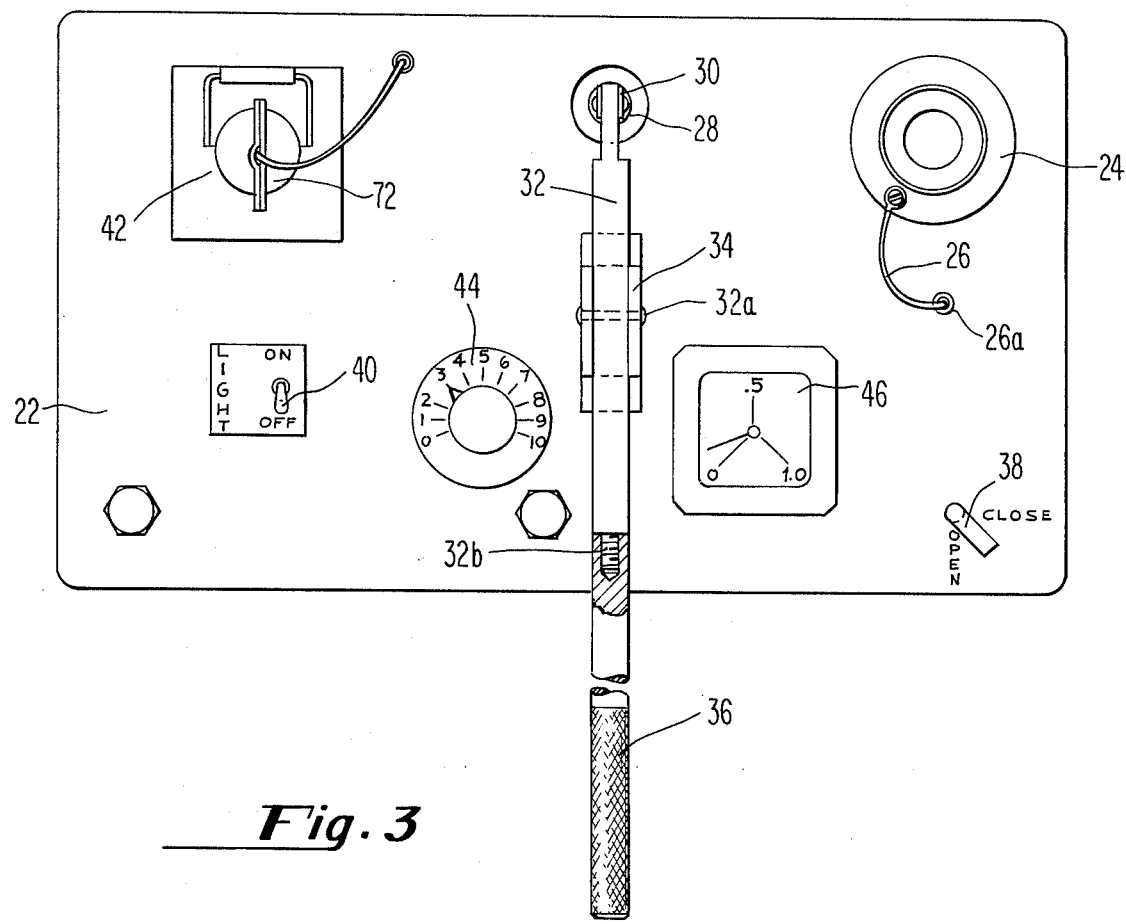
FIG. 3 is an enlarged plan view from above of the support deck removed from the casing showing structure attached to the deck and with the pump handle extension attached.

Referring now to FIG. 3, the view is one which is seen by the user looking down into the open casing of FIG. 2. The filter holder 24 is shown in place with its grounding lead 26 connected to the deck through jack 26A but the sample bottle is removed. Also visible are some of the parts of the pump actuator, which can also be seen in FIG. 2. However, FIG. 2 also shows the piston rod 28 and the parallel connecting links 30 which are pivotally connected at one end to the upper end of the piston rod and at the other end pivotally connected to the crossbar 32. Crossbar 32, in turn, is pivotally supported by pivot pin 32a extending across a forked fulcrum 34 supported on deck 22. Crossbar 32 is threaded at its free end 32b which is designed to engage the internally threaded tubular end of a removable handle extension 36, which is conveniently removed for storage. Removal of the extension permits closing up of the unit. The handle is readily re-assembled by making the threaded connection whereupon the pump is ready for use. Also available on the deck is a drain control handle 38 which enables a stopcock to be closed to permit establishing a vacuum in the vacuum fuel receptacle and then opens the fuel receptacle to permit drainage.

Also on the deck 22 is provided a light switch 40 which turns on and off the light associated with the photocell assembly 42. Intensity of the light is regulated by potentiometer 44 and its effect upon the photocell may be read on the milliammeter 46. In practice, the light intensity is set to a predetermined level on the meter 46 by the adjustment of the potentiometer 44 prior to making measurements of the two filter opacities.

Figure 4:
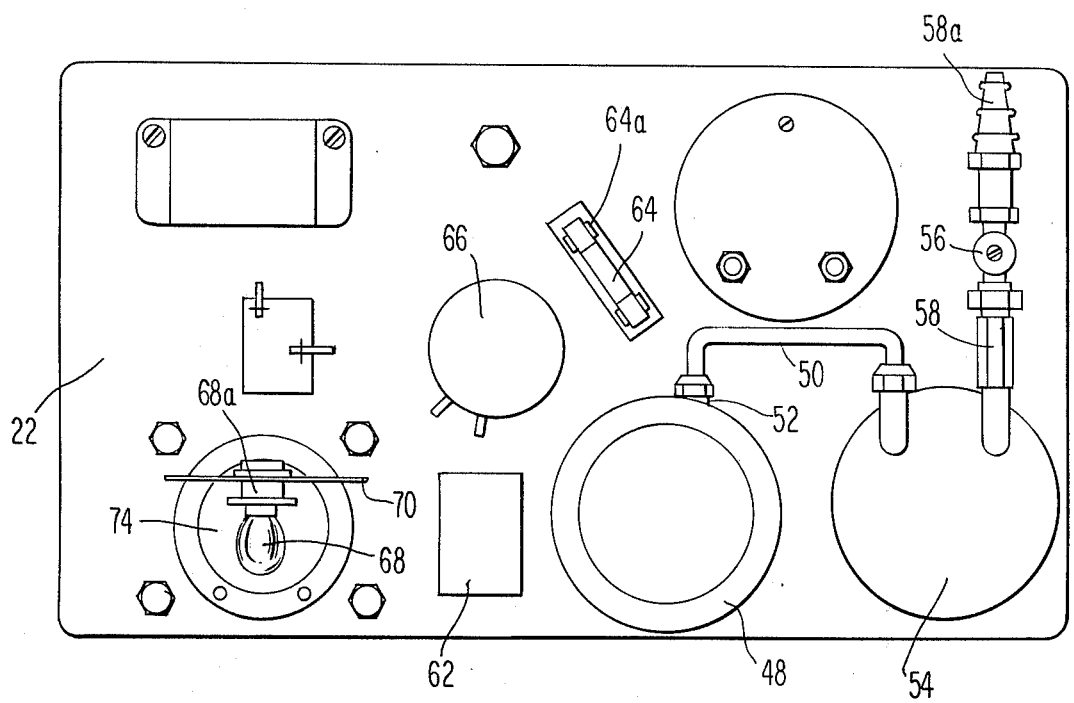
FIG. 4 is a similar plan view of the support deck from below, showing structure supported under the deck.

FIG. 4 shows the components on the underside of the deck 22. The pump cylinder 48 is vertically oriented and attached to the deck and connected by a vacuum line 50 through a check valve 52 to draw a vacuum in the vacuum fuel receptacle 54 when the stopcock 56 controlled by handle 38 (FIG. 3) is in closed position. When the stopcock is in open position, the vacuum fuel receptacle 54 may be drained of fuel through line 58 which is provided with a conventional fitting 58a at its end to receive a drain hose which may be attached and fed through a wall in the housing portion 10. Shutter closure 60, seen in FIG. 1, is rotated about its pivot 60a in housing 10 to permit exposure of the hole through housing 10 and use of the drain hose which, like the detachable pump handle 36, is carried within the cover portion 12, when not in use.

Electrically, in some models, there is provided a battery casing 62 which receives battery means and connects the battery means to power the photocell equipment. Alternatively, a power line can be provided for connection to an AC circuit. The alternating current may be used directly or with transformer means (not shown), depending upon the design of the instrumentation provided. Circuitry is not shown, but it will be understood that it is conventional and that suitable wiring is provided in required circuitry to connect together the batteries or other power source, the fuse 64 and fuse holder 64a, the potentiometer 66 and the light 68. The light 68 is supported and connected in circuitry light socket 68a supported, in turn, on the deck 22 by a suitable bracket 70. Also connected in circuit with the battery or other power source are the photocell 72 of the photocell assembly 42 and the meter 46, both seen in FIG. 3.

As a practical matter, the light 68 is positioned below a screen 74 on top of which the filters are placed for light opacity detections, after filtration, in accordance with practice known in the art. The light passing through each filter detected by the photocell establishes a reading on the milliammeter 46, and the differential current reading of the two series filters is then compared against a calibration to determine whether or not the fuel contamination level has reached or exceeded a predetermined rejection point, as is well-known practice in the prior art.

The filter holder 24 is basically a hollow tubular member consisting of two parts 24a and 24b (FIG. 5) which are preferably easily fitted together by some sort of quick twist lock arrangement and between which in a flat screen support portion the two series filter under test are held so that all fuel must pass through them. Two filters are used together in series so that the first filter will catch any contamination and the second will simply be colored by the fuel. In this way, the differential measurements may be made to correct for the light opacity effects of fuel color when measurements are taken. In this particular system, measurements are taken sequentially but in other systems simultaneous comparison of the filters might be made and arranged for direct readout of contamination.

Figure 5:
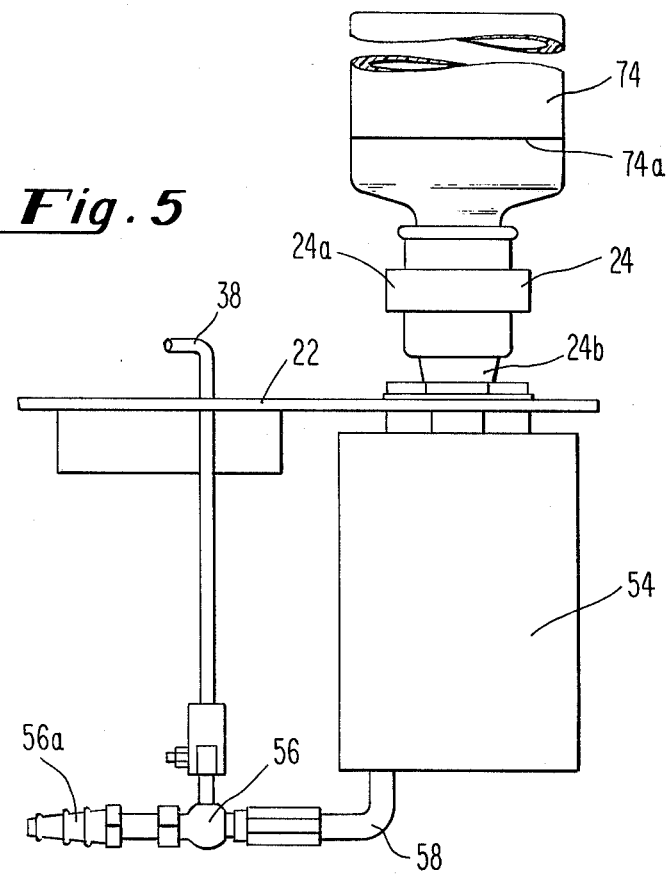
FIG. 5 is a schematic view showing the sample bottle, filter and vacuum receptacles, and the drain system of FIG. 4.

FIG. 5 also shows the positioning of the fuel sample bottle 74 and filter holder 24 in use. The sample bottle has a level mark for measurement of a standard quantity of liquid, say 600 ml. or 800 ml., by filling the bottle to this mark. In practice, the filters are placed in position in the filter holder 24 and the filter holder is inserted over the neck of the bottle 74. Before the bottle and filter combination is put in place, the drain handle 38 is turned to the closed position shutting the stopcock 56 and allowing a vacuum to be drawn. Thereafter, this whole assembly is inverted and the tapered resilient tubular portion of the filter holder bottom 24b is inserted tightly in a sealing neck of fuel receptacle 54, which completes a vacuum seal.

Figure 6:
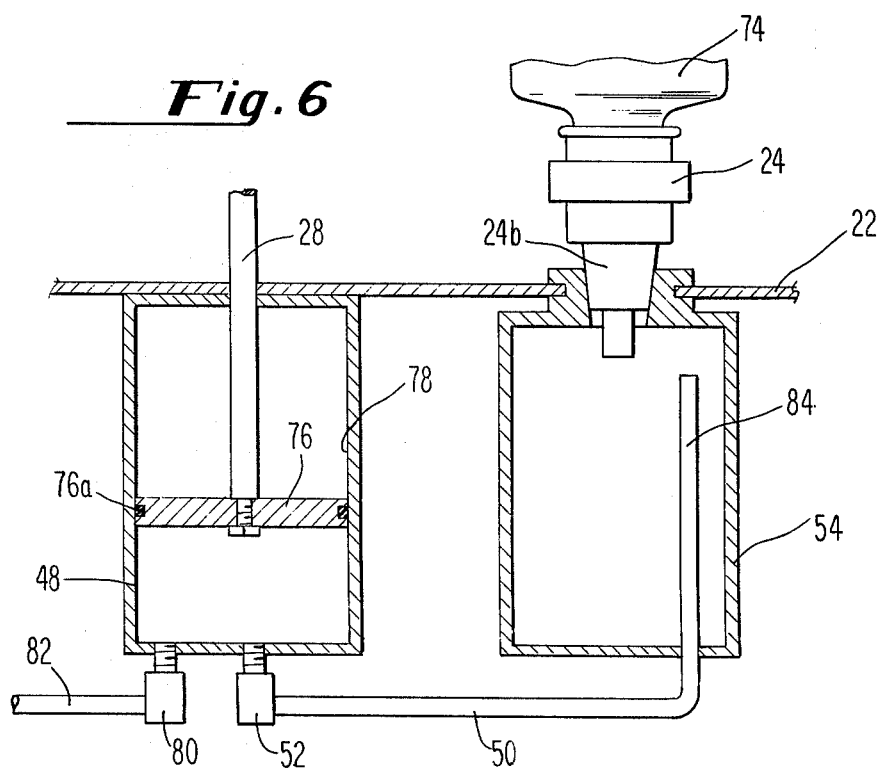
FIG. 6 is a schematic view showing the interrelationship of the pump and fuel vacuum chamber.

FIG. 6 shows the pumping action of piston 76 driven by a piston rod 28 within the hollow vertically oriented cylinder 78 of the pump 48. The piston has a sealing packing ring 76a. Downward motion of the piston 76 tends to force air out the bottom of the cylinder 78 through check valve 80 to exhaust line 82. As the piston is withdrawn valve 80 closes and valve 52 opens to permit the air or other gaseous contents of fuel chamber 54 to be withdrawn from above the liquid fuel level through vent tube 84 to the vacuum line 50 and hence through check valve 52 and to the cylinder 78 beneath the piston 76. Pumping should be begun promptly when the filter and bottle are placed in position in order to avoid any spillage of the fuel. The effect of the vacuum is, of course, to accelerate the passage of the fuel through two series filters, since gravity feed alone would take an unacceptably long period of time with membrane filters normally used to collect contamination.

The apparatus as described is put together in a novel compact arrangement which in addition to being compact is lightweight and highly portable. The specific arrangement shown is not necessarily critical but is highly desirable in that great efficiency has been achieved.

I claim:

1. In a portable contaminated fuel detector comprising at least sample holder means, fuel filter means in a filter retainer, a vacuum receptacle arranged in series with means causing said parts to seal together upon drawing a vacuum to accelerate flow of fuel through the filter means into the vacuum receptacle and vacuum pump means for said purpose connected by a vacuum line to said vacuum receptacle, the improvement comprising a box enclosure including a top and a bottom, a deck supported on said bottom for supporting, in turn, a photocell system, a meter coupled thereto, the vacuum chamber and vacuum pump, the vacuum pump being a hand-operated vacuum pump such that no electric power is needed to operate the vacuum pump including a vertically oriented cylinder parallel to and adjacent to the vacuum receptacle and containing a vertically-movable piston with sealing means between the cylinder and the edge of the piston and check valves between the vacuum chamber and pump preventing air return to the vacuum chamber and at the outlet preventing air return to the pump and an axially arranged piston rod, the deck supporting removable pieces such as the filter retainer and sample holder, the top cover enclosing parts projecting above the deck.

2. The portable contaminated fuel detector of claim 1 in which said deck supports a fulcrum element pivotally connected to a cross bar, a connecting linkage pivotally connected to the cross bar and pivotally connected to the piston rod and a removable handle extension, connectable to the other end of said cross bar.

3. The portable contaminated fuel detector of claim 2 in which all elements are closely positioned on said deck and the handle extension of the pump cross bar extends beyond the edge of the casing.

4. The portable contaminated fuel detector of claim 1 in which a battery receptacle is provided with circuit means to connect battery means placed therein into the photocell and meter circuit and into a circuit with a variable light source so that the entire device requires no outside power source.

* * * * *